United States Patent
Khoury

(10) Patent No.: US 7,722,538 B2
(45) Date of Patent: May 25, 2010

(54) CONDUCTANCE-IMAGING CATHETER AND DETERMINATION OF CAVITARY VOLUME

(75) Inventor: Dirar S. Khoury, 3227 Chesterfield La., Stafford, TX (US) 77477

(73) Assignee: Dirar S. Khoury, Stafford, TX (US)

( * ) Notice: Subject to any disclaimer, the term of this patent is extended or adjusted under 35 U.S.C. 154(b) by 986 days.

(21) Appl. No.: 11/351,588

(22) Filed: Feb. 10, 2006

(65) Prior Publication Data
US 2006/0178587 A1 Aug. 10, 2006

Related U.S. Application Data

(60) Provisional application No. 60/651,892, filed on Feb. 10, 2005.

(51) Int. Cl.
*A61B 8/00* (2006.01)
*A61B 5/05* (2006.01)

(52) U.S. Cl. ..................... 600/438; 600/547

(58) Field of Classification Search ......... 600/437–472, 600/509, 547
See application file for complete search history.

(56) References Cited

U.S. PATENT DOCUMENTS 4,674,518 A * 6/1987 Salo ........................... 600/508
6,112,115 A * 8/2000 Feldman et al. ............. 600/513
6,545,678 B1 * 4/2003 Ohazama ..................... 345/427

OTHER PUBLICATIONS

C Ding, L Rao, SF Nagueh, and DS Khoury, "Intracardiac Echocardiographic Measurement of Left Ventricular Volume," Proceedings of the 26th Annual International Conference of the IEEE EMBS, San Fransisco, CA, USA, Sep. 1-5, 2004, pp. 3662-3665.*

* cited by examiner

*Primary Examiner*—Long V Le
*Assistant Examiner*—Angela M Hoffa
(74) *Attorney, Agent, or Firm*—Law Offices of Mark L. Berrier

(57) ABSTRACT

Systems and methods for calibrating calculations based on catheter-originated measurements. One embodiment comprises a method for calibrating volume calculations for a fluid-filled cavity, such as a heart chamber. In this method, a first catheter configured to measure electrical characteristics and a second catheter configured to measure geometric characteristics are inserted into a fluid-filled cavity. Electrical characteristics of the fluid-filled cavity are measured with the first catheter and geometric characteristics of the cavity are measured with the second catheter. A volume segment is determined based on the measured geometric characteristics of the cavity, and a corresponding volume segment is determined based on the measured electrical characteristics of the cavity. Because the geometric calculation of the volume is known to be more accurate, the volume calculation based on the electrical measurements is adjusted (calibrated) to match the geometric calculation.

18 Claims, 7 Drawing Sheets

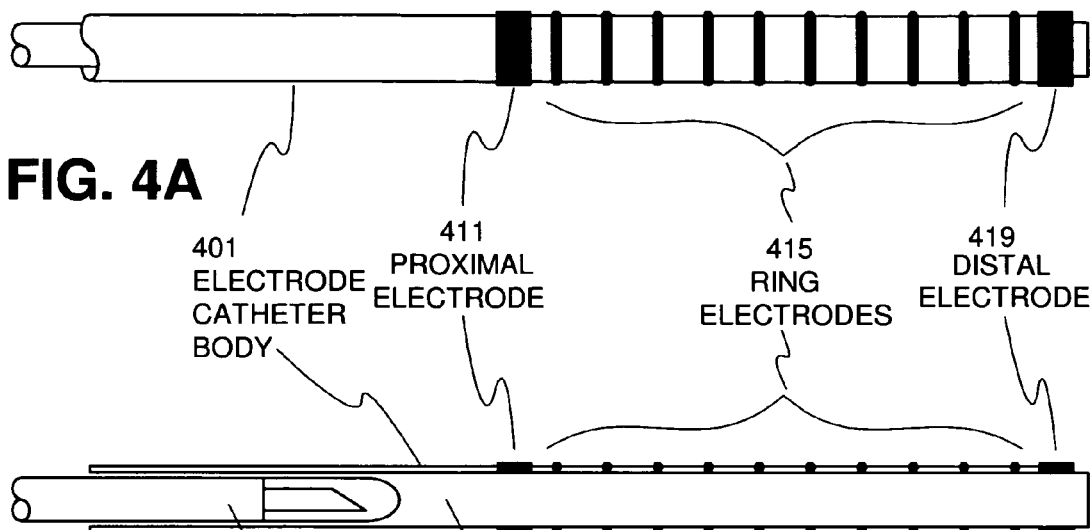
FIG. 4A
401 ELECTRODE CATHETER BODY
411 PROXIMAL ELECTRODE
415 RING ELECTRODES
419 DISTAL ELECTRODE
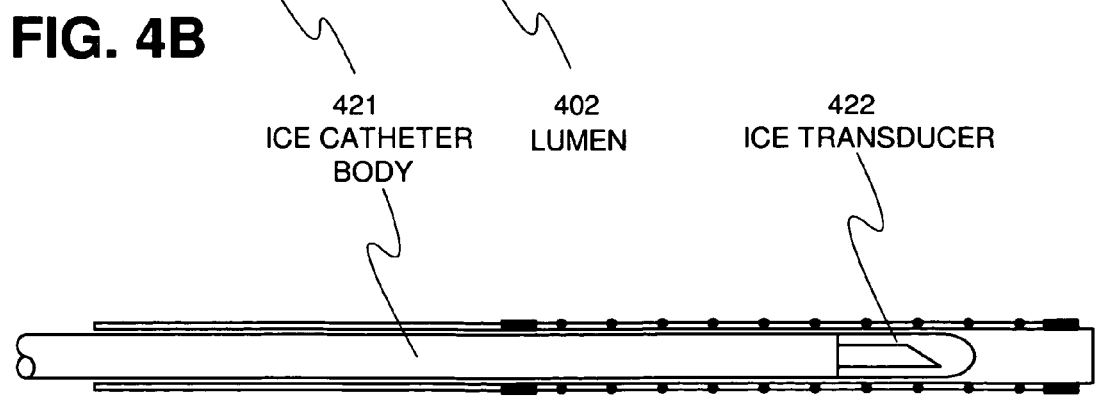
FIG. 4B
421 ICE CATHETER BODY
402 LUMEN
422 ICE TRANSDUCER
FIG. 4C

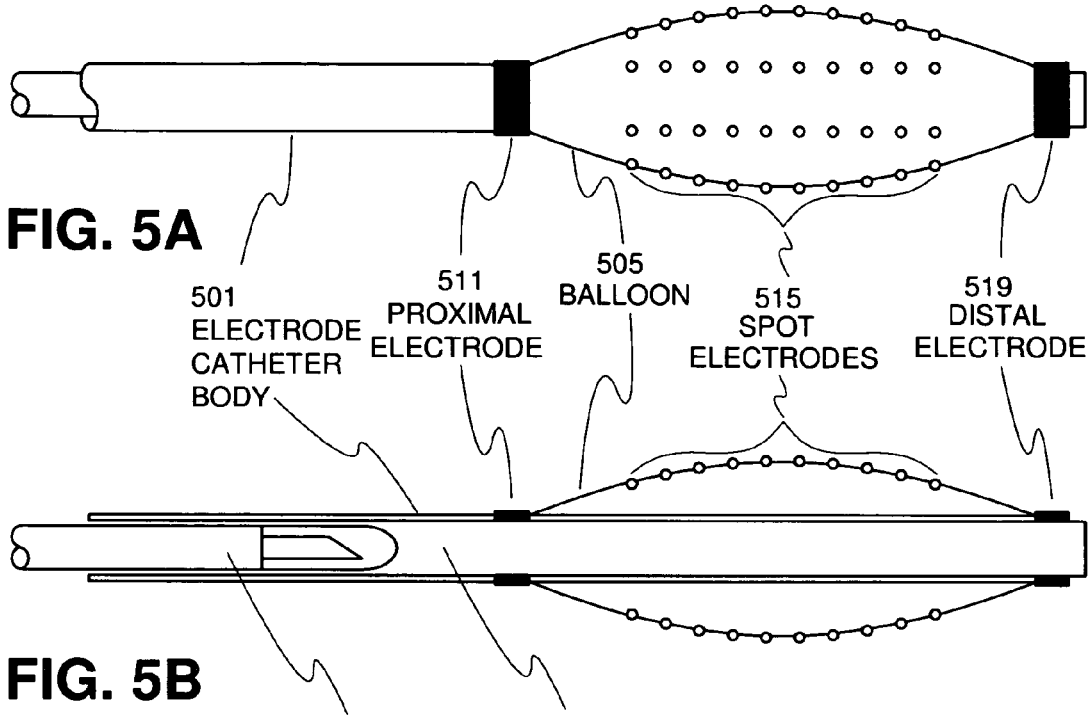

CONDUCTANCE-IMAGING CATHETER AND DETERMINATION OF CAVITARY VOLUME

CROSS-REFERENCE TO RELATED APPLICATIONS

This application claims the benefit of U.S. Provisional Application No. 60/651,892, filed Feb. 10, 2005, which is hereby incorporated by reference as if set forth herein in its entirety.

BACKGROUND

1. Field of the Invention

The invention involves systems and methods for calibrating measurements made by catheters usable in medical evaluations of a condition of a living body.

2. Related art

Evaluating cardiac function and hemodynamics is an integral component in managing patients with heart disease. Various invasive and noninvasive techniques have been used to assess volumes inside the hearts of these patients and include echocardiography, contrast angiography, radionuclide ventriculography, computed tomography, and magnetic resonance imaging.

However, none of these methods enables instantaneous and beat-by-beat assessment of cardiac cavitary volume.

A method for examining instantaneous changes in cavitary volume was previously developed on the basis of a conductance catheter carrying about 10 equidistant ring electrodes along the catheter shaft. The method involves delivering a very small alternating current between a pair of ring electrodes located at the distal and proximal ends of the catheter along the major axis of the heart cavity (such as the left ventricle), and recording resulting potentials between pairs of ring electrodes located on the catheter shaft between the current-delivering ring electrodes. Conductance (defined as 1/impedance) is the ratio of delivered current to measured varying potential. During the heartbeat, continuous changes in cavitary cross-sectional areas perpendicular to the catheter shaft (i.e. segmental volumes) cause instantaneous changes in conductance between catheter electrodes. Since injected current is fixed externally, measured potentials are inversely related to volume changes between recording electrode pairs. Hence, the conductance catheter method has been successfully used in recording instantaneous volume signals and assessing ventricular function. However, the conductance catheter method requires additional laborious steps for calibrating conductance signals into volume, which include (1) applying the thermodilution method to determine peak-to-peak change in cavitary volume (i.e. stroke volume), and (2) using the hypertonic saline infusion method to estimate a fixed value for parallel conductance brought about by electric current leakage into the myocardium and adjacent cavities. Calibration of conductance signals is adversely affected by procedural errors in these steps and by theoretical error in assuming constant parallel conductance effect throughout the heartbeat. Meanwhile, locations of current injecting and potential recording electrodes inside the heart cavity impacts the quality and accuracy of conductance signals. Yet, conductance signals have been predominantly recorded without accurate knowledge of electrode locations inside the heart cavity.

SUMMARY OF THE INVENTION

This disclosure is directed to systems and methods for calibrating calculations based on catheter-originated measurements that solve one or more of the problems discussed above.

One embodiment comprises a method for calibrating volume calculations for a fluid-filled cavity, such as a heart chamber. In this method, a first catheter configured to measure electrical characteristics and a second catheter configured to measure geometric characteristics are inserted into a fluid-filled cavity. Electrical characteristics of the fluid-filled cavity are measured with the first catheter and geometric characteristics of the cavity are measured with the second catheter. A volume segment is determined based on the measured geometric characteristics of the cavity, and a corresponding volume segment is determined based on the measured electrical characteristics of the cavity. Because the geometric calculation of the volume is known to be more accurate, the volume calculation based on the electrical measurements is adjusted (calibrated) to match the geometric calculation.

Another embodiment comprises a system having first and second catheters and a data correlation unit. The first catheter is configured to measure electrical characteristics within a fluid-filled cavity. The second catheter is configured to measure geometric characteristics of the cavity. The data correlation unit is coupled to the first and second catheters and is configured to correlate the electrical measurements from the first catheter with geometric measurements from the second catheter. The data correlation unit thereby calibrates data computed from the electrical measurements of the first catheter.

Numerous other embodiments are also possible.

BRIEF DESCRIPTION OF THE DRAWINGS

Other objects and advantages of the invention may become apparent upon reading the following detailed description and upon reference to the accompanying drawings.

FIGS. 4A-4C are diagrams illustrating the positioning of an ICE catheter within a conductance catheter in one embodiment.

FIGS. 5A-5C are diagrams illustrating the positioning of an ICE catheter within a conductance catheter in an alternative embodiment.

Figure 1:
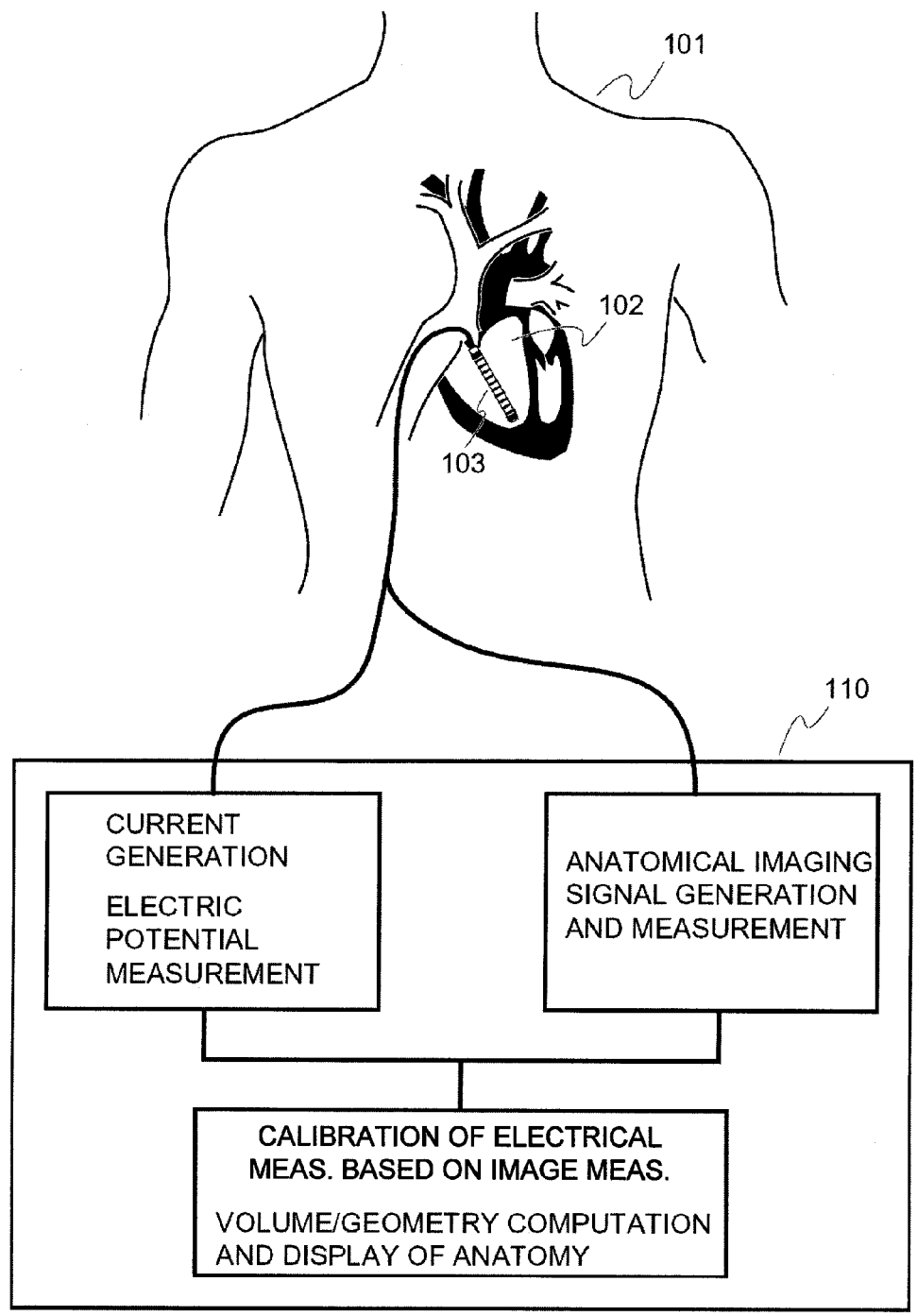
FIG. 1 is a diagram illustrating a conductance-imaging system in accordance with one embodiment.

While the invention is subject to various modifications and alternative forms, specific embodiments thereof are shown by way of example in the drawings and the accompanying detailed description. It should be understood, however, that the drawings and detailed description are not intended to limit the invention to the particular embodiment which is described. This disclosure is instead intended to cover all modifications, equivalents and alternatives falling within the scope of the present invention as defined by the appended claims.

DETAILED DESCRIPTION OF PREFERRED EMBODIMENTS

One or more embodiments of the invention are described below. It should be noted that these and any other embodiments described below are exemplary and are intended to be illustrative of the invention rather than limiting.

As described herein, various embodiments of the invention comprise systems and methods for calibrating measurements made by catheters usable in medical evaluations of a condition of a living body.

One or more embodiments of the invention are described below. It should be noted that these and any other embodiments described below are exemplary and are intended to be illustrative of the invention rather than limiting.

As described herein, various embodiments of the invention comprise systems and methods for calibrating measurements associated with the continuous determination of volume (geometry) using conductance and incorporating calibration data.

In one embodiment, an electrode catheter with a central lumen (a cavity within the catheter) is used in combination with an anatomical imaging device. These are used to make measurements of electric potential and geometry, respectively, when placed within a bounded conductive media (such as a blood-filled ventricle).

In this embodiment, an intracardiac echocardiographic (ICE) catheter is used for anatomical imaging and is positioned within the lumen of an electrode catheter. The combination is placed within a heart chamber. A current of known amplitude and frequency is injected from selected electrodes and measurements of electric potential taken at other electrodes. A volume segment of the heart chamber is then calculated from the measurements. Measurements are also made by the ICE catheter, and the volume segment is calculated from these measurements. (The ICE catheter is positioned to image the volume segment corresponding to a particular pair of electrodes.) The two partial volume computations are used to generate calibration data (e.g., a scaling factor) for subsequent volume calculations based on the electrical measurements of the electrode catheter. A conductance volume can then be determined and a final volume/geometry calculated incorporating calibration data based on the measurements from the ICE catheter.

Various embodiments of the invention will be described below. Primarily, these embodiments will focus on implementations comprising determination of a conductance volume and calculation of a final volume using calibration data determined using an intracardiac echocardiographic (ICE) catheter placed within the central lumen of an electrode/conductance catheter. The terms electrode catheter and conductance catheter are used interchangeably here. An electrode catheter used in determining conductance is often referred to as a conductance catheter.

It should be noted that these embodiments are intended to be illustrative rather than limiting, and alternative embodiments may be implemented. Many such variations will be apparent to persons of ordinary skill in the art of the invention and are intended to be encompassed by the appended claims.

FIG. 1 illustrates a conductance-imaging system in accordance with one embodiment. The system includes a catheter-system (103) and a data acquisition system (110). The system is illustrated in use in a human patient (101). The catheter-system is flexible and is percutaneously inserted through a blood vessel (vein or artery) for advancement into the blood-filled heart cavity (102). The catheter-system includes a lumen catheter with an array of electrodes on its surface and an anatomical imaging catheter located inside the lumen. The catheter-system enables a method to continuously detect volume properties of the heart cavity by activating the electrode array on its surface to measure electrical conductance of the blood volume. The system also enables a method to continuously detect geometrical properties of the heart's interior by inserting and operating an anatomical imaging catheter through the lumen. Both the conductance signals and the anatomical images are collected by the data acquisition system (110) that displays a calculated three-dimensional anatomy using calibration of the conductance signals based on geometrical information obtained by anatomical imaging.

Figure 2:
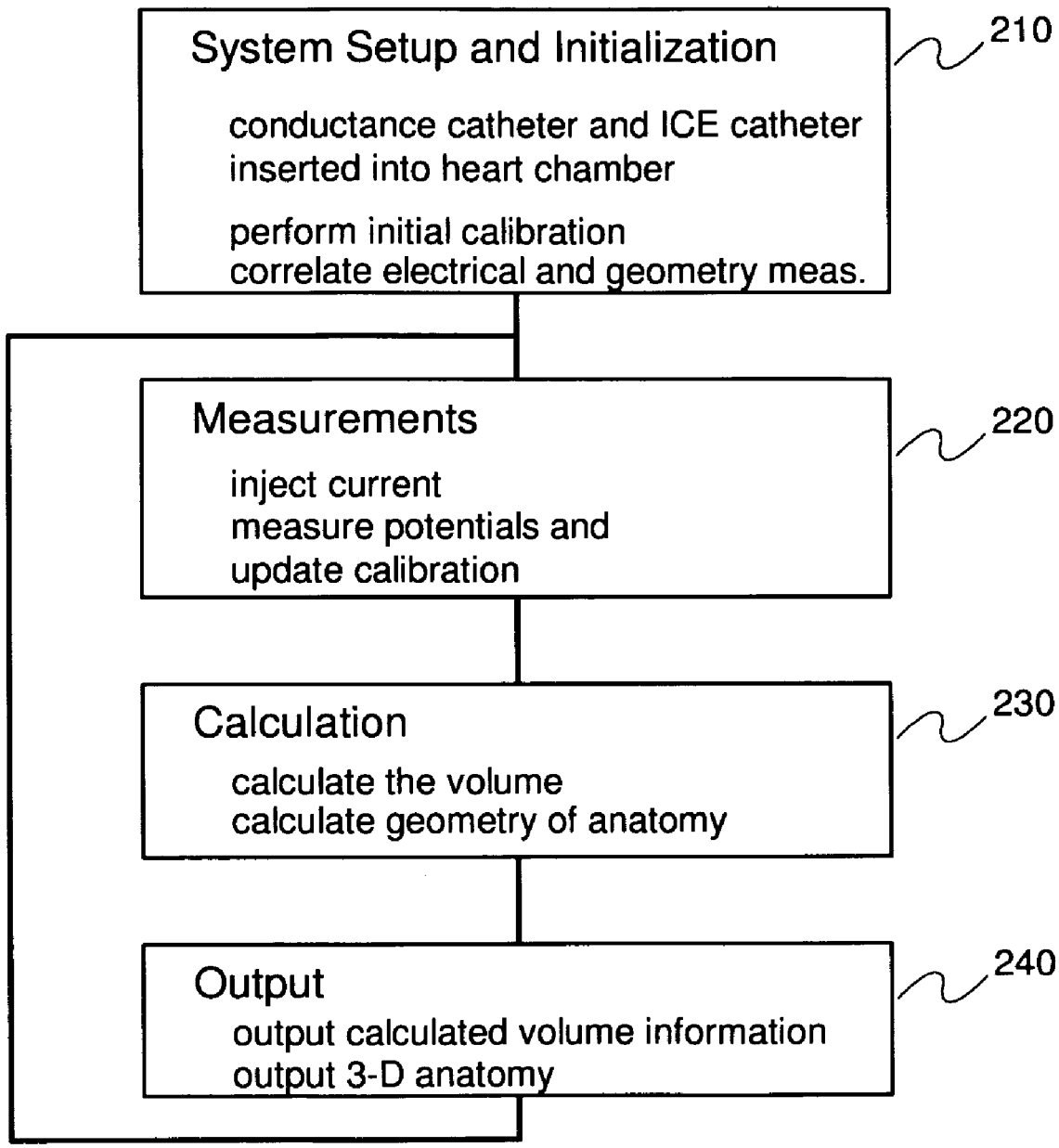
FIG. 2 is a flow diagram illustrating the operation of a system in accordance with one embodiment.

Referring to FIG. 2, a flow diagram illustrating the operation of a system in accordance with one embodiment is shown. The operation of the system begins with placement of an electrode catheter and an anatomical imaging catheter combination in a heart chamber (210). System initialization is also performed including initial calibration measurements. The system is then operated, injecting current and taking potential measurements (220), calculating the volume/geometry (230), displaying the result (240), and repeating (220, 230, 240). The measurements 220 can include updates to the calibration data.

Figure 3A:
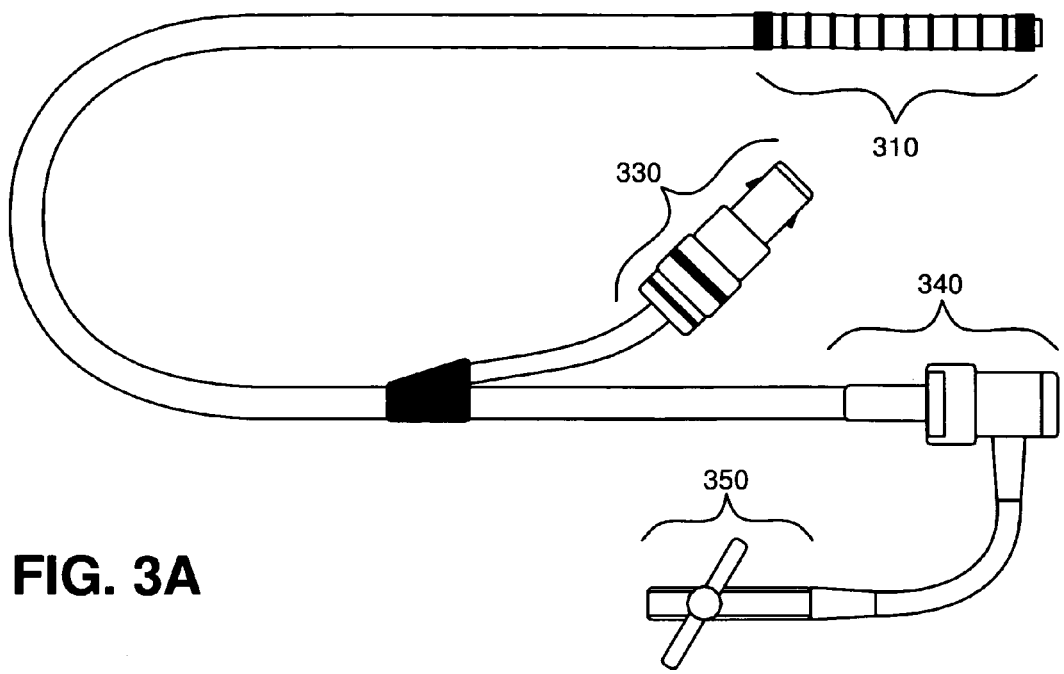
FIGS. 3A and 3B are a set of diagrams illustrating possible embodiments of a flexible conductance catheter having a central lumen.

Referring now to FIG. 3A, the conductance-imaging catheter-system of one embodiment includes a flexible lumen-catheter that carries a plurality of ring electrodes placed along the catheter shaft at its distal end (310). The electrodes enable measuring cavitary volumes by conductance. The lumen permits inserting an anatomical imaging catheter for determining the geometry of the heart's interior from inside the lumen. The lumen has an opening at the distal end. At its proximal end, the catheter includes a connector (330) that supplies electrical attachments to each of the ring electrodes. The catheter also includes at its proximal end a valve (340) that permits inserting an anatomical imaging catheter into the lumen and prevents backflow of cavitary blood. A 2-way stopcock valve (350) is attached at the proximal end of the catheter and provides access to the lumen to infuse or withdraw fluid.

Figure 3B:
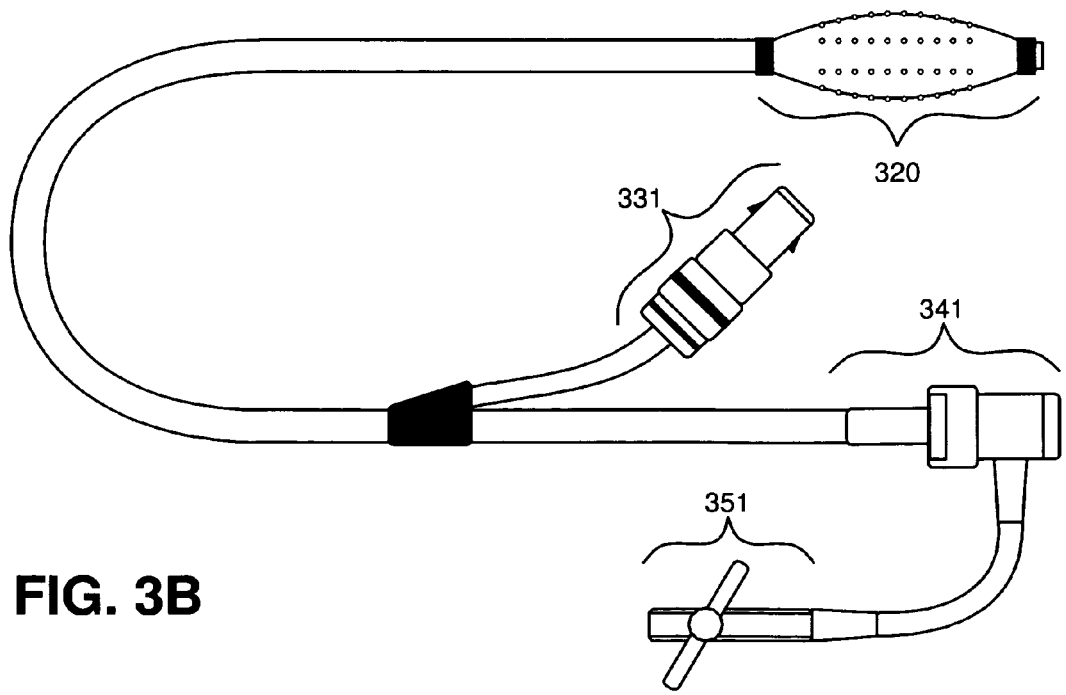

Referring now to FIG. 3B, a lumen-catheter of an alternate embodiment of the conductance-imaging catheter-system is illustrated in which a plurality of spot electrodes are laid on a central balloon (320) that is inflated to a fixed shape without the electrodes necessarily touching the interior surface of the heart. The spot electrodes are arranged in a fixed pattern over the balloon. The balloon has a continuous surface, is electrically nonconducting, and is similar to angioplasty catheters used in routine catheterization procedures. In its collapsed state, the size of the electrode array is similar to that of the catheter shaft. Thus, the operator is able to insert the catheter-system percutaneously and inflate the balloon inside the heart without occluding the cavity. The spot electrodes enable measuring cavitary volumes by conductance. A lumen passing through the balloon permits inserting an anatomical imaging catheter for determining the geometry of the heart's interior from inside the balloon. The lumen has an opening at the distal end. At its proximal end, the catheter includes a connector (331) that supplies electrical attachments to each of the spot electrodes. The catheter also includes at its proximal end a valve (341) that permits inserting an anatomical imaging catheter into the lumen and prevents backflow of cavitary blood. A 2-way stopcock valve (351) is attached at the proximal end of the catheter and provides access to the lumen to infuse or withdraw fluid.

FIG. 4A through FIG. 4C illustrate a portion of a conductance-imaging catheter-system in one embodiment. The portion of the system that receives the electrical and imaging data and correlates the data to calibrate calculation based on the conductance measurements (the data correlation unit) is not shown. FIGS. 4B and 4C are cutaways of the conductance catheter of FIG. 4A, exposing the central lumen and ICE catheter. The conductance catheter contains a central lumen 402 and an array of ring electrodes 415 located at the distal end of the catheter body 401. Electrical current is delivered between a distal electrode 419 and a proximal electrode 411 to produce an electrical field throughout the heart cavity. Multiple electrical potential signals are measured between pairs of ring electrodes 415 located on the catheter body 401 between distal electrode 419 and proximal electrode 411. The method of inserting an ICE catheter body 421 through the proximal end of lumen 402 of the electrode catheter is illustrated in FIGS. 4B and 4C. ICE catheter body 421 is advanced through the lumen 402 to the distal end of the electrode catheter as illustrated in FIG. 4C. The ICE transducer 422 at the tip of the ICE catheter is enabled to acquire cross-sectional anatomical images of the heart's interior through the catheter wall from within the lumen 402 between ring electrodes 415. The ring electrodes 415 (as well as 411 and 419) serve as markers for determining the location of the ICE transducer 422 by yielding a distinct image when the ICE transducer is operated directly from under a ring electrode. Multiple cross-sectional anatomical images, containing geometrical information on the location of the electrode catheter and the heart's interior, are usually obtained by pulling the ICE catheter back from the distal electrode 419 to the proximal electrode 411 at fixed increments and at a resolution on the order of 1 mm. Multiple continuous ICE images acquired between a pair of recording ring electrodes are added together to yield a segment volume that correlates with conductance between the same pair of electrodes. The method of calibrating conductance signals is performed according to the following:

$C$=Delivered Current/Measured Potential $C = m \cdot \text{Vol} + b$ $m = (\text{Vol}_{max} - \text{Vol}_{min})/(C_{max} - C_{min})$ $b = [\text{Vol}_{max} \cdot (C_{max} - C_{min}) - C_{max} \cdot (\text{Vol}_{max} - \text{Vol}_{min})] / (C_{max} - C_{min})$ where C is segmental conductance signal measured between a pair of ring electrodes, Vol is actual segmental volume determined at the same time during the heartbeat by ICE and between the same pair of electrodes, $C_{min}$ and $C_{max}$ are minimum and maximum segmental conductance values during the heartbeat, respectively, and $\text{Vol}_{min}$ and $\text{Vol}_{max}$ are minimum and maximum cavitary segmental volumes bounded by a pair of ring electrodes and determined by ICE during the heartbeat, respectively.

As noted above, the data correlation unit is not shown in the figures. The data correlation unit may be implemented in any suitable type of data processor, such as a personal computer. Alternatively, the data correlation unit may be implemented in application-specific hardware, such as an ASIC (application-specific integrated circuit,) or in a programmable DSP (digital signal processor.) Because the implementation and programming of the data correlation unit will be readily apparent to a person of ordinary skill in the field of the invention, this will not be described in detail here.

FIG. 5A through FIG. 5C illustrate the electrical/imaging catheter portion of an alternate embodiment of the conductance-imaging catheter-system. FIGS. 5B and 5C are cutaways of the conductance catheter of FIG. 5A, exposing the central lumen and ICE catheter. The conductance catheter contains a central lumen 502 and an array of electrodes located at the distal end of the electrode catheter body 501. The electrodes include a distal ring electrode 519, a proximal ring electrode 511, and spot electrodes 515 arranged in a fixed pattern over an inflatable balloon. The method of inserting the ICE catheter body 521 through the proximal end of lumen 502 of the electrode catheter is illustrated in FIG. 5B. ICE catheter body 521 is advanced through the lumen 502 to the distal end of the electrode catheter as illustrated in FIG. 5C. The ICE transducer 522 at the tip of the ICE catheter is enabled to acquire anatomical images of the heart's interior through the balloon 505. Activating the ICE transducer directly from under a distal ring electrode 519 or proximal ring electrode 511 yields a distinct image that serves as a marker for determining the location of the ICE transducer 522 inside the lumen 502. (The spot electrodes do not interfere with the imaging.) Multiple cross-sectional anatomical images, containing geometrical information on the location of the electrode catheter and the heart's interior, are usually obtained by pulling the ICE catheter back from the distal ring electrode 519 to the proximal ring electrode 511 at fixed increments and at a resolution on the order of 1 mm. Multiple continuous ICE images are added together to yield segment volumes.

Figure 6:
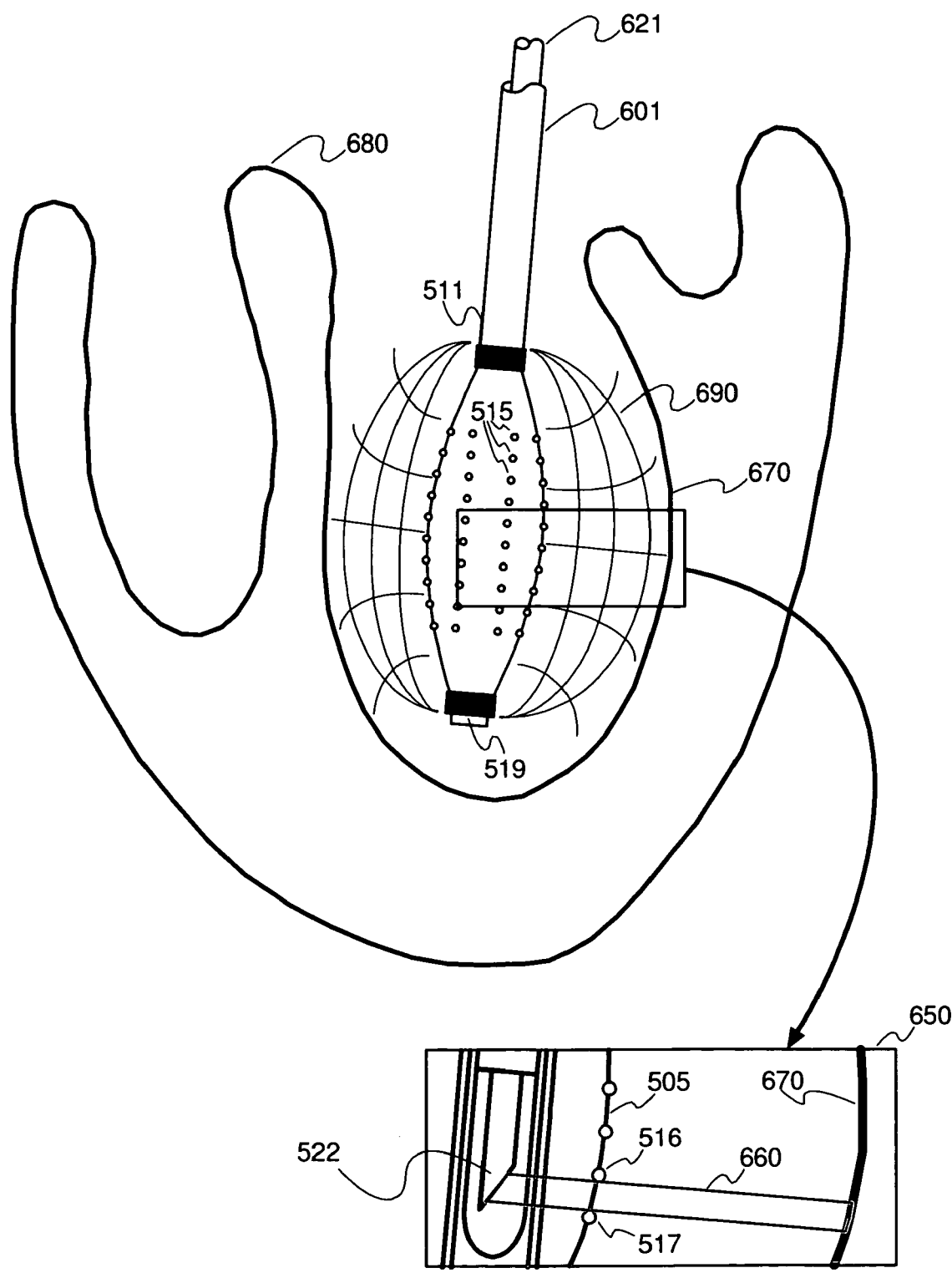
FIG. 6 is a diagram illustrating the catheter portion of a conductance-imaging catheter system of one embodiment inserted within a chamber of a heart.

Referring now to FIG. 6, illustrated is the catheter portion of a conductance-imaging catheter-system of one embodiment inserted within a chamber of a heart. The conductance catheter electrodes include a distal ring electrode 519, a proximal ring electrode 511, and an array of spot electrodes 515 arranged in a fixed pattern over an inflatable balloon. Within a central lumen is an ICE catheter. The ICE catheter is exposed in inset 650. The ICE transducer 522 at the tip of the ICE catheter acquires anatomical images of the heart's interior through the balloon 505. The anatomical image is a cross-section 660 taken from the ICE transducer 522 to the heart wall 670. This ICE data will be correlated with measurements taken with electrodes 516 and 517.

In one method, electric current 690 is injected between distal ring electrode 519 and proximal ring electrode 511. Electric potential is measured between the equivalent of ring electrodes created by averaging the potentials at multiple spot electrodes on the same row around the balloon. Averaging of potential is performed either numerically or by attaching together the corresponding electrode pins at the proximal connector end of the catheter. The method of calibrating the conductance signals is performed according to the following:

$C$=Delivered Current/Measured Potential $C = m \cdot \text{Vol} + b$ $m = (\text{Vol}_{max} - \text{Vol}_{min})/(C_{max} - C_{min})$ $b = [\text{Vol}_{max} \cdot (C_{max} - C_{min}) - C_{max} \cdot (\text{Vol}_{max} - \text{Vol}_{min})] / (C_{max} - C_{min})$ As noted above, C is segmental conductance signal measured between a pair of ring electrodes, Vol is actual segmental volume determined at the same time during the heartbeat by ICE and between the same pair of electrodes, $C_{min}$ and $C_{max}$ are minimum and maximum segmental conductance values during the heartbeat, respectively, and $\text{Vol}_{min}$ and $\text{Vol}_{max}$ are minimum and maximum cavitary segmental volumes bounded by a pair of ring electrodes and determined by ICE during the heartbeat, respectively.

An alternate method to measure conductance signals associated with different regions of the heart cavity is to inject electric current between a pair of spot electrodes located on the same column along the balloon. The method is repeated for each of the columns of spot electrodes around the balloon, either simultaneously using electric currents with different non-overlapping characteristics for each column, or in sequence using current pulses. Corresponding potentials are measured simultaneously at spot electrodes either along the same column or on different columns.

An alternate method to determine cavitary volume by the conductance technique is to inject electric current between a pair of electrodes on the electrode catheter 601. Laplace's equation ($\nabla^2 V=0$) is applied to describe the electric potential in the volume between the surface of electrode catheter 601 and the interior surface of the heart. Current injecting electrodes (sources and sinks) are modeled as boundary conditions at select regions on the electrode catheter, and the rest of the electrode catheter as well as the heart are subject to the Neumann boundary condition of zero current at the surface. The standard boundary element numeric method is employed to solve Laplace's equation and determine a relationship between the potentials on the catheter and on the heart surfaces. Accordingly, a set of simultaneous equations is constructed of the form: $HU=GQ$, where H and G are n×n matrices that are dependent on the cavity geometry, and U and Q are vectors of length n representing potentials and fluxes (respectively) at sampling points in the model (n is the total number of points). Therefore, an algorithm for determining dynamic cavitary volume operates by first estimating cavitary geometry by ICE at one time instant during the cardiac cycle. Electric current is injected by either ring or spot electrodes on the electrode catheter, and corresponding potentials are measured by the catheter spot electrodes. Electrode sites where current is injected are used as boundary conditions, and electric potentials are numerically computed on the electrode catheter and on the heart surface by the boundary element method. The geometry of the heart surface is then numerically and iteratively altered throughout the cardiac cycle to provide an optimal fit between measured and computed potentials on the electrode catheter. Dynamic cavitary geometry is derived throughout the cardiac cycle by converging at each time instant to a prespecified error tolerance.

The method of operating the conductance-imaging catheter-system to measure conductance by an electrode catheter and volume by an imaging catheter may be used to determine conductivity (or resistivity) of the blood-filled medium.

The conductivity between a pair of ring electrodes of the conductance catheter may be computed according to: $\mu = C \cdot L^2 / \text{Vol}$, where C is measured conductance, L is the distance between the pair of ring electrodes, and Vol is the segmental volume bounded by the pair of ring electrodes as determined by ICE.

Figure 7:
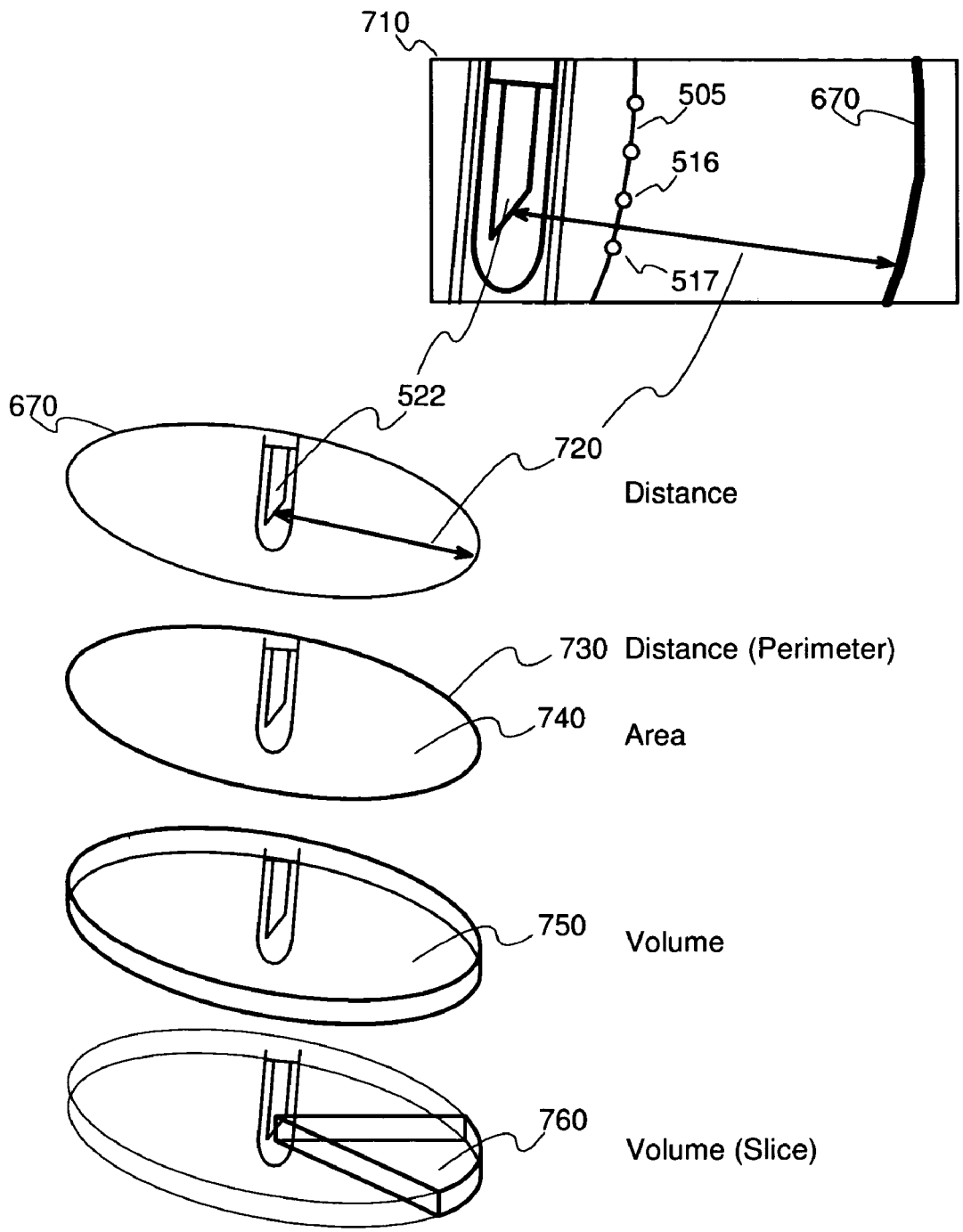
FIG. 7 is a diagram illustrating several exemplary geometric parameters determined from anatomic images acquired by an ICE transducer that may be employed in calibrating conductance signals.

Referring now to FIG. 7, illustrated are several exemplary geometric parameters determined from anatomic images acquired by the ICE transducer 522 that may be employed in calibrating conductance signals. These include: (1) distance 720 between the transducer 522 and the heart wall 670, (2) perimeter 730 of the heart wall 670 and cavitary cross-sectional area 740 around the transducer 522 at any level in the heart cavity, (3) cavitary segment volume 750 obtained by pulling the ICE transducer 522 a fixed distance and integrating multiple cross-sectional areas 740 along the path, and (4) cavitary sector (slice) volume 760 obtained by pulling the ICE transducer 522 a fixed distance and integrating multiple areas bounded by sectors of known angular coverage along the path.

While the foregoing description presents several specific exemplary embodiments, there may be many variations of the described features and components in alternative embodiments. For example, the calibration and volume determination may be performed in other types of fluid-filled cavities, other types of catheters may be used to obtain the electrical and geometric data, various different algorithms may be used to perform the necessary calculations, calculations other than volumes may be made the basis of the calibration, and so on. Many other variations will also be apparent to persons of skill in the art of the invention upon reading the present disclosure.

Those of skill in the art will understand that information and signals may be represented using any of a variety of different technologies and techniques. For example, data, information, signals, and the like that may be referenced throughout the above description may be represented by voltages, currents, electromagnetic waves, or any combination thereof. The information and signals may be communicated between components of the disclosed systems using any suitable transport media, including wires, metallic traces, vias, optical fibers, and the like.

Those of skill will further appreciate that the various illustrative logical blocks, modules, circuits, and algorithm steps described in connection with some embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Those of skill in the art may implement the described functionality in varying ways for each particular application, but such implementation decisions should not be interpreted as causing a departure from the scope of the present invention.

The steps of a method or algorithm described in connection with the embodiments disclosed herein may be embodied directly in hardware, in software (program instructions) executed by a processor, or in a combination of the two. Software may reside in RAM memory, flash memory, ROM memory, EPROM memory, EEPROM memory, registers, hard disk, a removable disk, a CD-ROM, or any other form of storage medium known in the art. Such a storage medium containing program instructions that embody one of the present methods is itself an alternative embodiment of the invention. One exemplary storage medium may be coupled to a processor, such that the processor can read information from, and write information to, the storage medium. In the alternative, the storage medium may be integral to the processor.

The benefits and advantages which may be provided by the present invention have been described above with regard to specific embodiments. These benefits and advantages, and any elements or limitations that may cause them to occur or to become more pronounced are not to be construed as critical, required, or essential features of any or all of the claims. As used herein, the terms "comprises," "comprising," or any other variations thereof, are intended to be interpreted as non-exclusively including the elements or limitations which follow those terms. Accordingly, a system, method, or other embodiment that comprises a set of elements is not limited to only those elements, and may include other elements not expressly listed or inherent to the claimed embodiment.

While the present invention has been described with reference to particular embodiments, it should be understood that the embodiments are illustrative and that the scope of the invention is not limited to these embodiments. Many variations, modifications, additions and improvements to the embodiments described above are possible. It is contemplated that these variations, modifications, additions and improvements fall within the scope of the invention as detailed within the following claims.

What is claimed is:

1. A method of determining volume of a fluid-filled cavity comprising:
    inserting into the fluid-filled cavity a device configured to measure electrical characteristics and geometric characteristics;
    measuring one or more electrical characteristics and one or more geometric characteristics of the fluid-filled cavity with the device;
    determining a first value for a volume for at least a first portion of the fluid-filled cavity based on the measured geometric characteristics of the fluid-filled cavity;
    determining a second value for the volume for the first portion of the fluid-filled cavity based on the measured electrical characteristics of the fluid-filled cavity;
    generating a calibration data using the first and second values for the volume of the fluid-filled cavity; and
    determining a subsequent volume of the fluid-filled cavity based on the electrical measurements and the calibration data.

2. The method of claim 1, wherein the device comprises a first conductance catheter configured to measure electrical characteristics and a second intracardiac echography catheter to measure geometric characteristics, the method further comprising positioning the intracardiac echography catheter within a central lumen of the conductance catheter and measuring the geometric characteristics of the fluid-filled cavity from within the central lumen of the conductance catheter.

3. The method of claim 1, wherein the step of measuring the one or more electrical characteristics is performed by a first catheter and the step of measuring the one or more geometric characteristics is performed by a second catheter.

4. The method of claim 1, wherein the device comprises a first catheter configured to measure electrical characteristics and a second catheter configured to measure geometric characteristics, wherein measuring one or more electrical characteristics of the fluid-filled cavity comprises applying a current across proximal and distal electrodes of the first catheter and measuring potential between one or more pairs of intermediate electrodes.

5. The method of claim 4, wherein applying the current across the proximal and distal electrodes comprises applying an alternating current.

6. The method of claim 5, wherein the current is alternated at two or more frequencies.

7. The method of claim 4, wherein applying the current across the proximal and distal electrodes comprises applying a sequence of square pulses.

8. The method of claim 1, wherein the one or more electrical characteristics and the one or more geometric characteristics of the fluid-filled cavity are measured at substantially the same instant in time.

9. The method of claim 1, wherein the physical characteristic of the fluid-filled cavity is a segmental volume of the cavity, wherein the segmental volume of the cavity is less than the total volume of the cavity, and wherein the measured electrical characteristics and geometric characteristics are associated with the segmental volume of the cavity.

10. A system for determining volume of a fluid-filled cavity comprising:
    a measurement unit configured to measure electrical characteristics and geometric characteristics within a fluid-filled cavity; and
    a data correlation unit coupled to the measurement unit and configured to:
        determine a first value for a volume for at least a first portion of the fluid-filled cavity based on the measured geometric characteristics of the fluid-filled cavity;
        determine a second value for the volume for the first portion of the fluid-filled cavity based on the measured electrical characteristics of the fluid-filled cavity;
        generate a calibration data using the first and second values for the volume of the fluid-filled cavity; and
        determine a subsequent volume of the fluid-filled cavity based on the electrical measurements and the calibration data.

11. The system of claim 10, wherein the measurement unit comprises a first catheter configured to measure electrical characteristics and a second catheter configured to measure geometric characteristics.

12. The system of claim 11, wherein the first catheter comprises a conductance catheter and the second catheter comprises an intracardiac echography catheter, wherein the conductance catheter has a central lumen therein, and wherein the intracardiac echography catheter is configured to be positioned within the central lumen of the conductance catheter and to measure the geometric characteristics of the fluid-filled cavity from within the central lumen of the conductance catheter.

13. The system of claim 11, wherein the first catheter includes proximal and distal electrodes and one or more pairs of intermediate electrodes positioned between the proximal and distal electrodes, wherein the first catheter is configured to provide measurements of potentials induced between the one or more pairs of intermediate electrodes.

14. The system of claim 13, further comprising an alternating current source coupled to the proximal and distal electrodes to apply a current across the proximal and distal electrodes.

15. The system of claim 14, wherein the alternating current source is configured to alternate the current at two or more frequencies.

16. The system of claim 14, wherein the alternating current source is configured to apply the current as a sequence of square pulses.

17. The system of claim 10, wherein the measurement unit is configured to measure the electrical characteristics and the geometric characteristics within the fluid-filled cavity at substantially the same instant in time.

18. The system of claim 10, wherein the electrical characteristics and the geometric characteristics are characteristics of a segmental volume of a cavity.

* * * * *